United States Patent
Gallop et al.

(10) Patent No.: US 10,470,825 B2
(45) Date of Patent: Nov. 12, 2019

(54) METHOD, SYSTEM AND APPARATUS FOR SURFACE RENDERING USING MEDICAL IMAGING DATA

(71) Applicant: SYNAPTIVE MEDICAL (BARBADOS) INC., Bridgetown (BB)

(72) Inventors: David Bruce Gallop, Toronto (CA); Sean Jy-Shyang Chen, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/678,529

(22) Filed: Aug. 16, 2017

(65) Prior Publication Data
US 2019/0053853 A1 Feb. 21, 2019

(51) Int. Cl.
| | | |
|---|---|---|
| *A61B 34/20* | (2016.01) | |
| *A61B 34/00* | (2016.01) | |
| *A61B 5/00* | (2006.01) | |
| *A61B 34/10* | (2016.01) | |
| *G06T 15/06* | (2011.01) | |
| *G06T 17/00* | (2006.01) | |

(52) U.S. Cl.
CPC ............ *A61B 34/20* (2016.02); *A61B 5/0035* (2013.01); *A61B 34/25* (2016.02); *A61B 2034/107* (2016.02)

(58) Field of Classification Search
CPC ....... A61B 34/20; A61B 34/25; A61B 5/0035; A61B 2034/107
See application file for complete search history.

(56) References Cited

U.S. PATENT DOCUMENTS

| | | |
|---|---|---|
| 6,266,453 B1 | 6/2001 | Hibbard et al. |
| 6,687,527 B1 | 2/2004 | Wu et al. |
| 7,231,076 B2 | 6/2007 | Fu et al. |
| 7,327,865 B2 | 2/2008 | Fu et al. |

(Continued)

FOREIGN PATENT DOCUMENTS

| | | |
|---|---|---|
| EP | 3358528 A1 | 8/2018 |
| EP | 3358529 A2 | 8/2018 |

OTHER PUBLICATIONS

Search Report issued by the Intellectual Property Office of the United Kingdom in relation to the corresponding GB application No. GB1813208.4 dated Feb. 15, 2019, 5 pgs.

*Primary Examiner* — Charles E Anya
(74) *Attorney, Agent, or Firm* — Perry + Currier Inc.

(57) ABSTRACT

A method, system and apparatus for surface rendering using medical imaging data is provided. A display device is controlled to render a first model of imaging data showing depth positions corresponding to a given surface threshold value, and further controlled to replace the first model with a second model of the imaging data showing respective depth positions corresponding to the given surface threshold value, the second model being faster to compute than the first model. The given surface threshold value is changed to an updated surface threshold value, for example using a slider input. The display device updates rendering of the second model to show updated respective depth positions corresponding to the updated surface threshold value. When an acceptance is received, the display device is controlled to replace the second model with the first model showing updated depth positions corresponding to the updated surface threshold value.

16 Claims, 16 Drawing Sheets

(56) References Cited

U.S. PATENT DOCUMENTS

| | | | |
|---|---|---|---|
| 7,366,278 B2 | 4/2008 | Fu et al. | |
| 10,062,185 B2* | 8/2018 | Kelly | G06T 11/008 |
| 2003/0147505 A1 | 8/2003 | Numata et al. | |
| 2004/0009459 A1 | 1/2004 | Anderson et al. | |
| 2015/0213646 A1* | 7/2015 | Ma | G06T 17/20 |
| | | | 345/420 |
| 2015/0235085 A1* | 8/2015 | Goto | G06K 9/00624 |
| | | | 382/103 |
| 2016/0364907 A1* | 12/2016 | Schoenberg | G06T 17/205 |
| 2018/0108169 A1* | 4/2018 | Miller | G06T 15/08 |
| 2018/0180688 A1* | 6/2018 | Koch | G01R 33/243 |

* cited by examiner

METHOD, SYSTEM AND APPARATUS FOR SURFACE RENDERING USING MEDICAL IMAGING DATA

FIELD

The specification relates generally to medical imaging, and specifically to a method, system and apparatus for surface rendering using medical imaging data.

BACKGROUND

Minimally invasive surgical techniques can reduce the risk of injury to patients, in comparison with traditional surgical techniques. However, accurate surface rendering (e.g. skin, cortical surfaces and the like) at an image rendering device can be critical when planning a surgery and/or performing a skin or brain surface based registration during a navigated procedure. Such surfaces may be determined based on the contents of a volumetric magnetic resonance (MR) imaging scan or computerized tomography scan using an algorithm that determines portions of imaging data that represent patient tissue and portions that represent regions adjacent patient tissue (e.g. air/hair/padding etc.). While such algorithms may do a reasonable job of extracting a surface, errors in the imaging data may cause the algorithms to inaccurately extract a surface. For example, in MR imaging, signal inhomogeneity may lead to a "cratered" skin surface appearance in the rendering of the imaging data. While this can be addressed by forcing the extraction algorithm to use a lower threshold value to extract a surface, the imaging datasets are generally very large and models used to extract surfaces must be carefully refined surgical purposes, causing the image rendering device to operate inefficiently when the extraction is performed repeatedly. For example, even a single adjustment to a threshold value may require the imaging device to use tens of seconds to re-determine a surface, and the imaging device will not be able to provide any indication of whether the adjustment was successful until the algorithm has completed. This causes the image rendering device to operate inefficiently, especially when several adjustments to the threshold value are made to achieve an acceptable result.

SUMMARY

An aspect of the specification provides a device comprising: a memory storing imaging data, the imaging data comprising three-dimensional imaging data of an object; a display device; an input device; and a controller configured to: control the display device to render a first model of the imaging data showing depth positions corresponding to a given surface threshold value; control the display device to replace the first model with a second model of the imaging data showing respective depth positions corresponding to the given surface threshold value, the second model being faster to compute than the first model; receive, from the input device, input changing the given surface threshold value e to an updated surface threshold value, and control the display device to update rendering of the second model to show updated respective depth positions corresponding to the updated surface threshold value; receive, from the input device, an acceptance of the updated surface threshold value; and control the display device to replace the second model with the first model showing updated depth positions corresponding to the updated surface threshold value.

Another aspect of the specification provides a method comprising: controlling, using a controller, a display device to render a first model of imaging data showing depth positions corresponding to a given surface threshold value, the imaging data comprising three-dimensional imaging data of an object; controlling, using a controller, the display device to replace the first model with a second model of the imaging data showing respective depth positions corresponding to the given surface threshold value, the second model being faster to compute than the first model; receiving, at the controller, from an input device, input changing the given surface threshold value to an updated surface threshold value, and controlling, using the controller, the display device to update rendering of the second model to show updated respective depth positions corresponding to the updated surface threshold value; receiving, at the controller, from the input device, an acceptance of the updated surface threshold value; and controlling, using the controller, the display device to replace the second model with the first model showing updated depth positions corresponding to the updated surface threshold value.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
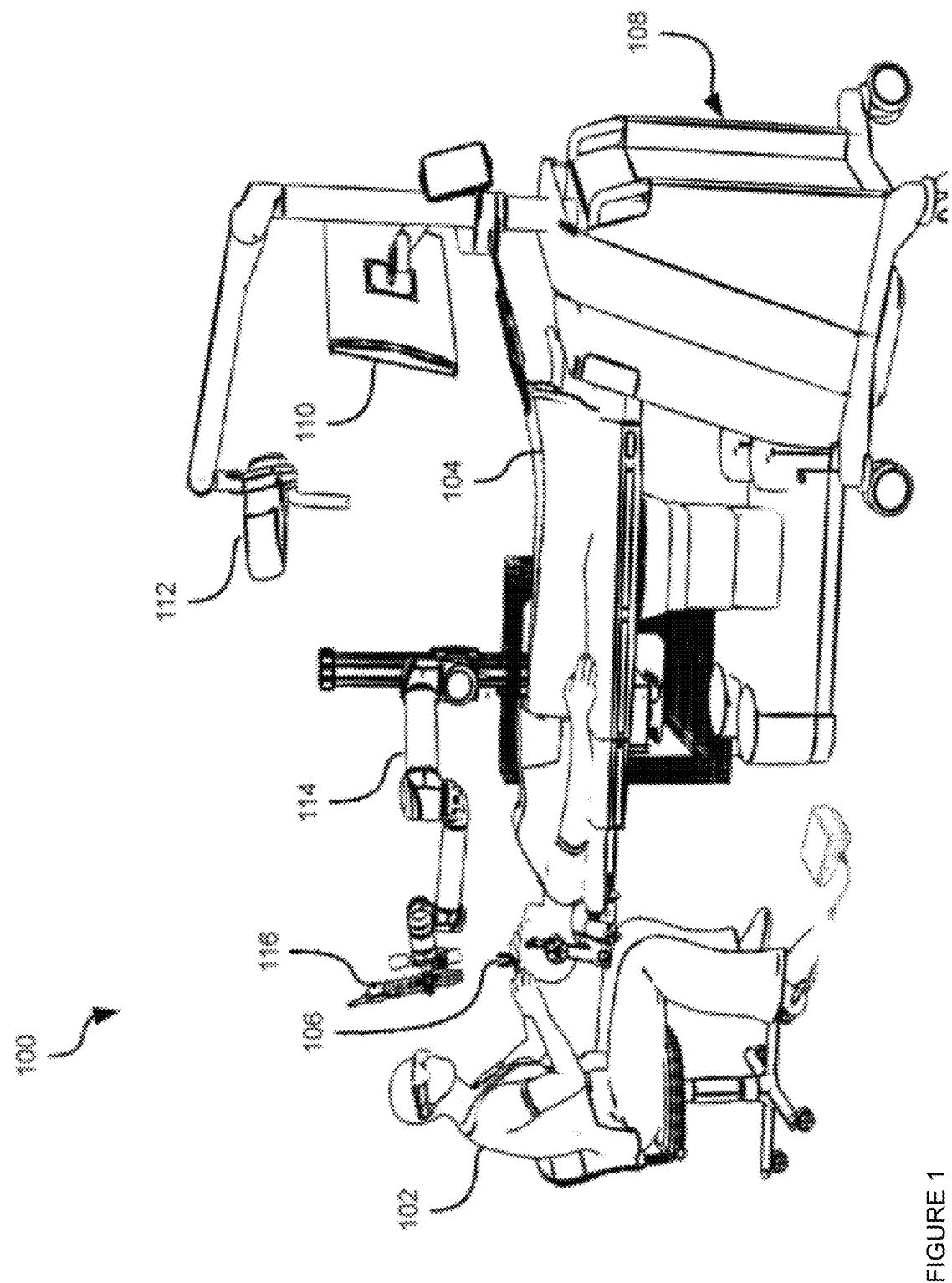
FIG. 1 depicts an operating theatre, according to a non-limiting embodiment.

FIG. 1 depicts a system 100 that includes a surgical operating theatre in which a healthcare worker, for example a surgeon 102 operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. The description below makes reference to the brain of patient 104 as an example of tissue to which the techniques herein may be applied. It will be understood, however, that those techniques may also be applied to a wide variety of other tissues. Thus, when the brain of patient 104 is mentioned below, it is simply an example of the various tissues in connection with which the systems and methods herein may be implemented.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the sulcal folds of the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as at least one display device 110 connected to the computing device for displaying images provided by the computing device.

Equipment tower 108 also supports a tracking system 112. Tracking system 112 is generally configured to track the positions of one or more reflective markers (not shown) mounted on access port 106, any of the above-mentioned surgical tools, or any combination thereof. Such markers, also referred to as fiducial markers, may also be mounted on patient 104, for example at various points on the head of patient 104. Tracking system 112 may therefore include a camera (e.g. a stereo camera) and a computing device (either the same device as mentioned above or a separate device) configured to locate the fiducial markers in the images captured by the camera, and determine the spatial positions of those markers within the operating theatre. The spatial positions may be provided by tracking system 112 to the computing device in equipment tower 108 for subsequent use.

The nature of the markers and the camera are not particularly limited. For example, the camera may be sensitive to infrared (IR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. The predefined locations, as well as the geometry of each tracked object, are configured within tracking system 112, and thus tracking system 112 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 106 by robotic arm 114, and may capture images of the brain of patient 104 for presentation on display device 110. The movement of robotic arm 114 to place external scope 116 correctly over access port 106 may be guided by tracking system 112 and the computing device in equipment tower 108. The images from external scope 116 presented on display device 110 may be overlaid with other images, including images obtained prior to the surgical procedure. The images presented on display device 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images may be collected of patient 104, or at least of patient 104's brain or portions thereof. Such preoperative images may be collected using any of a variety of imaging modalities, such as Magnetic Resonance Imaging (MM), Optical Coherence Tomography (OCT), ultrasound, Computed Tomography (CT), optical spectroscopy and the like. For each of the above-mentioned imaging modalities, various imaging techniques may be used. Polarization Sensitive OCT and OCT elastography are exemplary uses of the OCT modality. Diffusion MRI (also referred to as diffusion tensor imaging, DTI) is an example use of the MM modality. Raman spectroscopy is an example use of optical spectroscopy. A variety of other examples of the above modalities will also occur to those skilled in the art.

Preoperative images may be used for planning purposes. During the procedure, additional images (referred to as intraoperative images) may be collected of the brain of patient 104, using any suitable ones of the above-mentioned modalities (it will be apparent to those skilled in the art that some imaging modalities are less suitable or unsuitable for preoperative use, while other imaging modalities are less suitable or unsuitable for intraoperative use).

An example of a planning activity that may be performed using preoperative images is the selection of entry locations and trajectories for surgical tools through the patient tissue (e.g., the brain of patient 104) to a target, such as a tumour to be resected. As will be apparent to those skilled in the art, surgical tools such as access port 106 may reach targeted areas via a wide variety of trajectories from the outer surface of the brain or other tissue. Some of those trajectories may be more suitable than others, for example due to reduced interference with cortical tissue, vascular tissue, or the like. As will be described in further detail below, the computing device housed in equipment tower 108 can perform various actions to process and render medical imaging data such as the above-mentioned preoperative images, selecting and implementing visual filters to distinguish between tissue types in the images.

Figure 2:
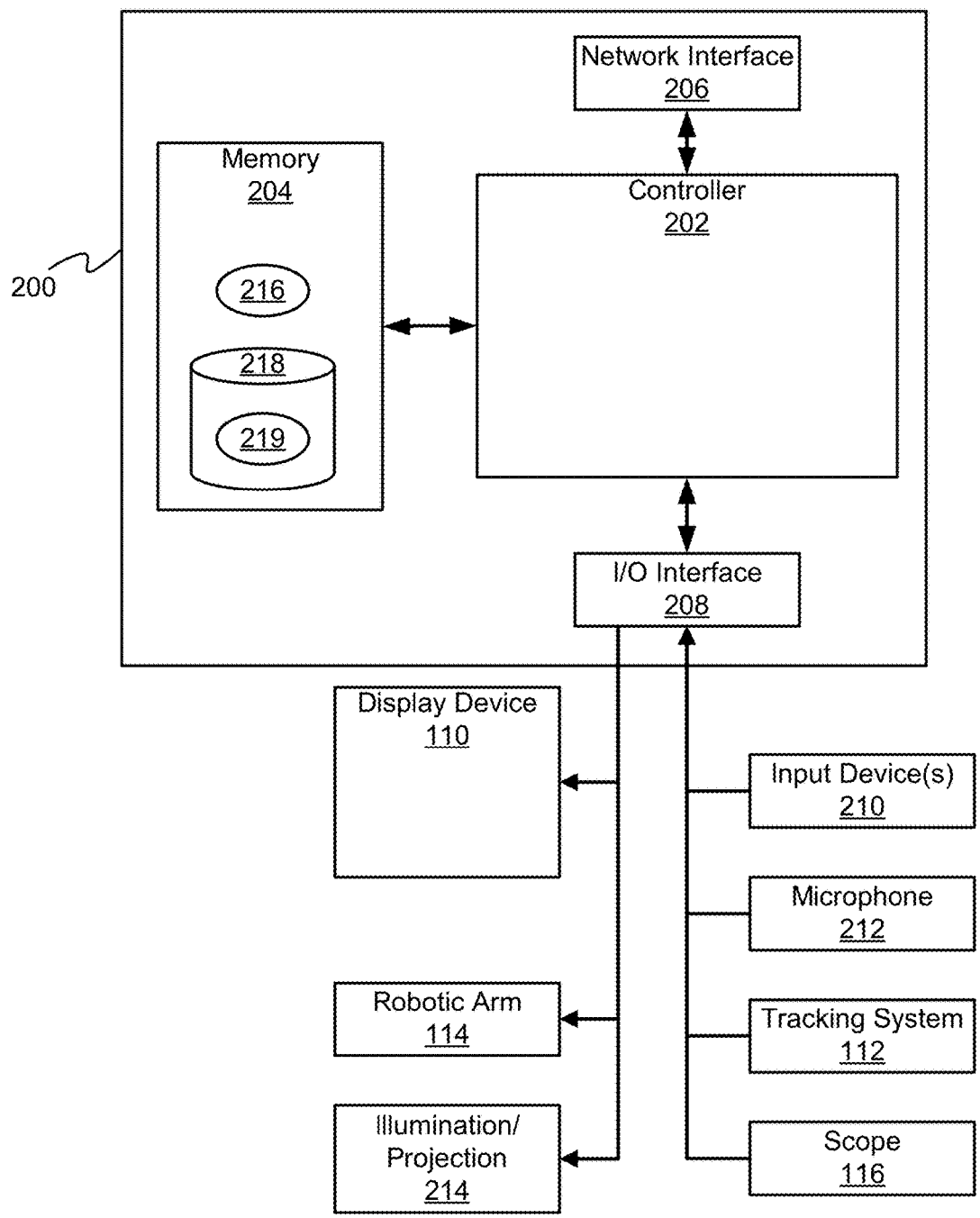
FIG. 2 depicts a computing device of the operating theatre of FIG. 1, according to a non-limiting embodiment.

Before a discussion of the functionality of the computing device, a brief description of the components of the computing device will be provided. Referring to FIG. 2, a computing device 200 is depicted, including controller 202 interconnected with a non-transitory computer readable storage medium such as a memory 204.

Controller 202 can comprise a processor and/or a plurality of processors, including but not limited to one or more central processors (CPUs) and/or one or more processing units; either way, controller 202 comprises a hardware element and/or a hardware processor. Indeed, in some embodiments, controller 202 can comprise an ASIC (application-specific integrated circuit) and/or an FPGA (field-programmable gate array) specifically configured to implement specific projection mapping previsualization functionality. Hence, device 200 is preferably not a generic computing device, but a device specifically configured to implement specific surface rendering functionality and/or image rendering functionality and/or medical imaging functionality. For example, device 200 and/or controller 202 can comprise a computer executable engine configured to implement specific surface rendering functionality and/or medical imaging functionality.

Hence, controller 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 also includes a network interface 206 interconnected with controller 202. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 also includes an input/output interface 208, including the necessary hardware for interconnecting controller 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to one or more input devices 210 such as a keyboard and mouse, a microphone 212, as well as scope 116 and tracking system 112, mentioned above. Also via interface 208, computing device 200 is connected to output devices including illumination or projection components 214 (e.g. lights, projectors and the like), as well as display device 110 and robotic arm 114 mentioned above. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 200 via network interface 206.

Computing device 200 stores, in memory 204, a surface extraction application 216 (also referred to herein as application 216) comprising a plurality of computer readable instructions executable by controller 202. When controller 202 executes the instructions of application 216 (or, indeed, any other application stored in memory 204), controller 202 performs various functions implemented by those instructions, as will be discussed below. Controller 202, or computing device 200 more generally, is therefore said to be "configured" or "operating" to perform those functions via the execution of application 216.

Also stored in memory 204 are various data repositories, including a patient data repository 218. Patient data repository 218 can contain a surgical plan defining the various steps of the minimally invasive surgical procedure to be conducted on patient 104, as well as imaging data relating to patient 104, such as MRI and CT scans, three-dimensional images of the brain of patient 104, and the like. In the present embodiment, repository 218 includes at least imaging data 219 comprising three-dimensional imaging data and/or volumetric imaging data, and specifically of a volume of patient tissue having an outer surface, such as the skin of a patient and/or the brain of patient 104. Indeed, the term "outer surface" as used herein may not refer only to an absolute outer surface of the patient (e.g. a patient's skin), but also to the outer surface of an object within the patient, such as the patient's brain. While imaging data 219 will be described herein with respect to magnetic resonance imaging data (MR imaging data), processes described herein can be applied to three-dimensional imaging data acquired using three-dimensional imaging technique.

Figure 3:
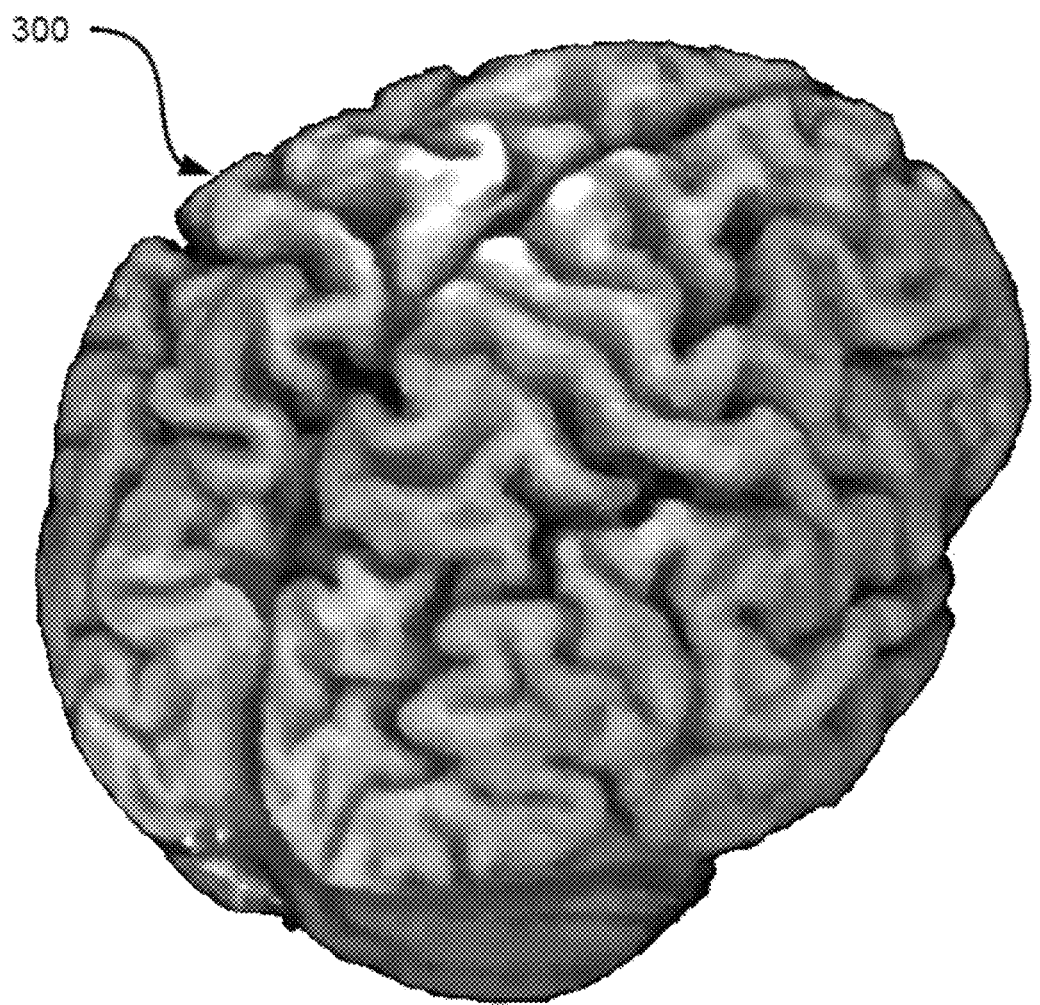
FIG. 3 depicts an image of a volume of tissue maintained by the computing device of FIG. 2, according to a non-limiting embodiment.

Referring to FIG. 3, an example image 300 of a volume of tissue stored in repository 218 is depicted, for example in imaging data 219. The volume of tissue is the brain of patient 104 in the present example, and image 300 is a three-dimensional image of the brain of patient 104 obtained via MM scanning. As seen in FIG. 3, image 300 depicts an outer surface of the brain. Image 300 also includes image data depicting various internal structures of the brain (not visible in FIG. 3), and may further include image data depicting structures surrounding the brain (such as the skull of patient 104). In other words, the patient tissue depicted by the image 300 depicts a plurality of different tissue types.

Figure 4:
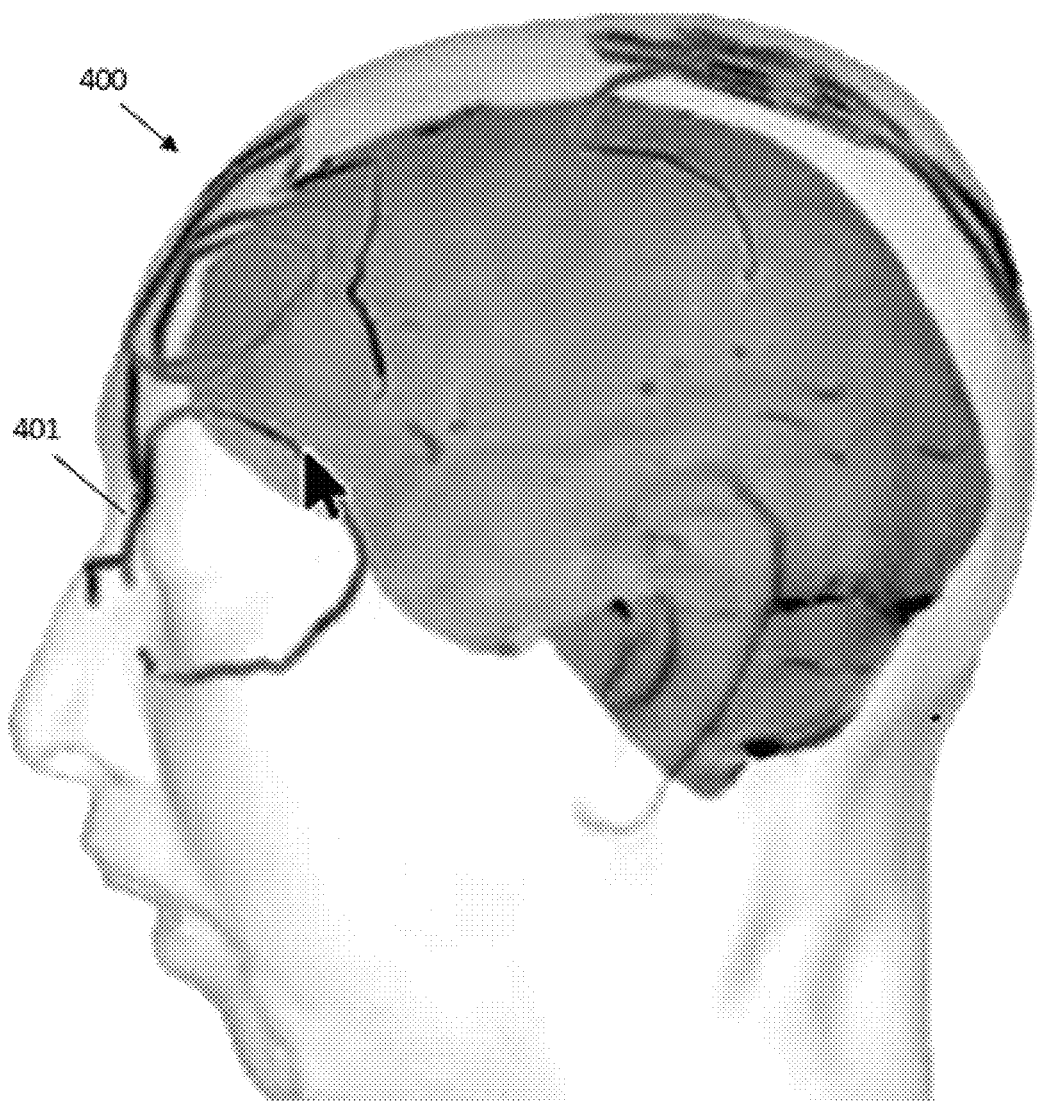
FIG. 4 depicts another image of a volume of tissue maintained by the computing device of FIG. 2, according to a non-limiting embodiment.

Similarly, referring to FIG. 4 another example image 400 of a volume of tissue stored in repository 218 is depicted, for example in imaging data 219. The volume of tissue is the head of patient 104 in the present example, and image 400 is a three-dimensional image of the head of patient 104, as obtained via MM scanning. As seen in FIG. 4, image 400 depicts an outer surface of the head. Image 400 also includes image data depicting various internal structures of the brain, and may further include image data depicting structures surrounding the brain (such as the skull of patient 104). In other words, as in the image 300, the patient tissue depicted by the image 400 depicts a plurality of different tissue types.

Also depicted in FIG. 4 are markers 401 that have been overlaid on image 400 that indicate the outer surface of the head of patient 104, markers 401 representative of physical markers placed on the head of patient 104 during surgery. In other words, for accurate placement of markers 401 on image 400, rendering of skin of patient 104 has to be somewhat accurate as either the placement of markers 401 becomes inaccurate (which may make surgical planning difficult and/or dangerous) and/or impossible. Put another way, the markers 401 are rendered at the image 400 assuming that that skin on which corresponding physical markers are located has been registered at image 400 such that optical images of patient 104 captured during surgery using an optical camera (that include the physical markers) are aligned with image 400. Such imaging techniques used in surgery hence rely on an accurate identification of a skin surface in image 400. A similar issue may be present in image 300 when physical markers are placed on the surface of the brain of patient 104, which are to be registered at the image 300.

Figure 5:
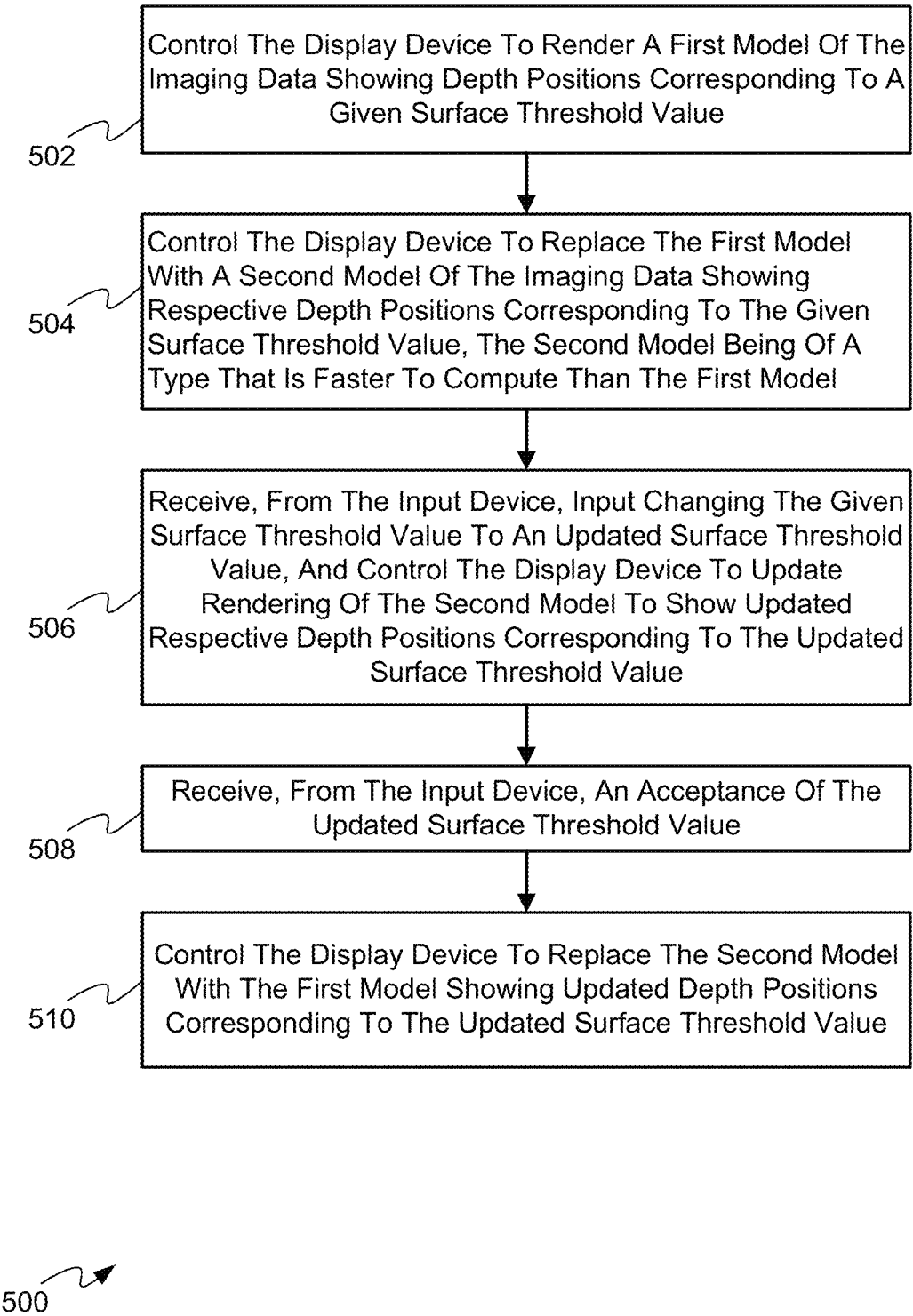
FIG. 5 depicts a method of surface rendering using medical imaging data, according to a non-limiting embodiment.

Turning to FIG. 5, a method 500 of surface rendering using medical imaging data is depicted. Method 500 will be discussed in connection with its performance in system 100, and particularly by the computing device 200, via the execution of application 216 by controller 202. As will be discussed in greater detail below, via the performance of method 500, computing device 200 is configured to render imaging data 219 and update a surface threshold value using two models of the imaging data 219.

At a block 502, the controller 202 controls the display device 110 to render a first model of the imaging data 219 showing depth positions corresponding to a given surface threshold value (for example, an expected skin surface, an expected brain surface, and the like).

At a block 504, the controller 202 controls the display device 110 to replace the first model with a second model of the imaging data 219 showing respective depth positions corresponding to the given surface threshold value. In general, the second model is of a type that is faster to compute and/or implement than the first model.

At a block 506, the controller 202 receives, from the input device 210, input changing the given surface threshold value to an updated surface threshold value, and control the display device 110 to update rendering of the second model to show updated respective depth positions corresponding to the updated surface threshold value.

At a block 508, the controller 202 receives, from the input device 210, an acceptance of the updated surface threshold value.

At a block 510, the controller 202 controls the display device 110 to replace the second model with the first model showing updated depth positions corresponding to the updated surface threshold value.

Method 500 will now be discussed with reference to FIG. 6 to FIG. 16.

Figure 6:
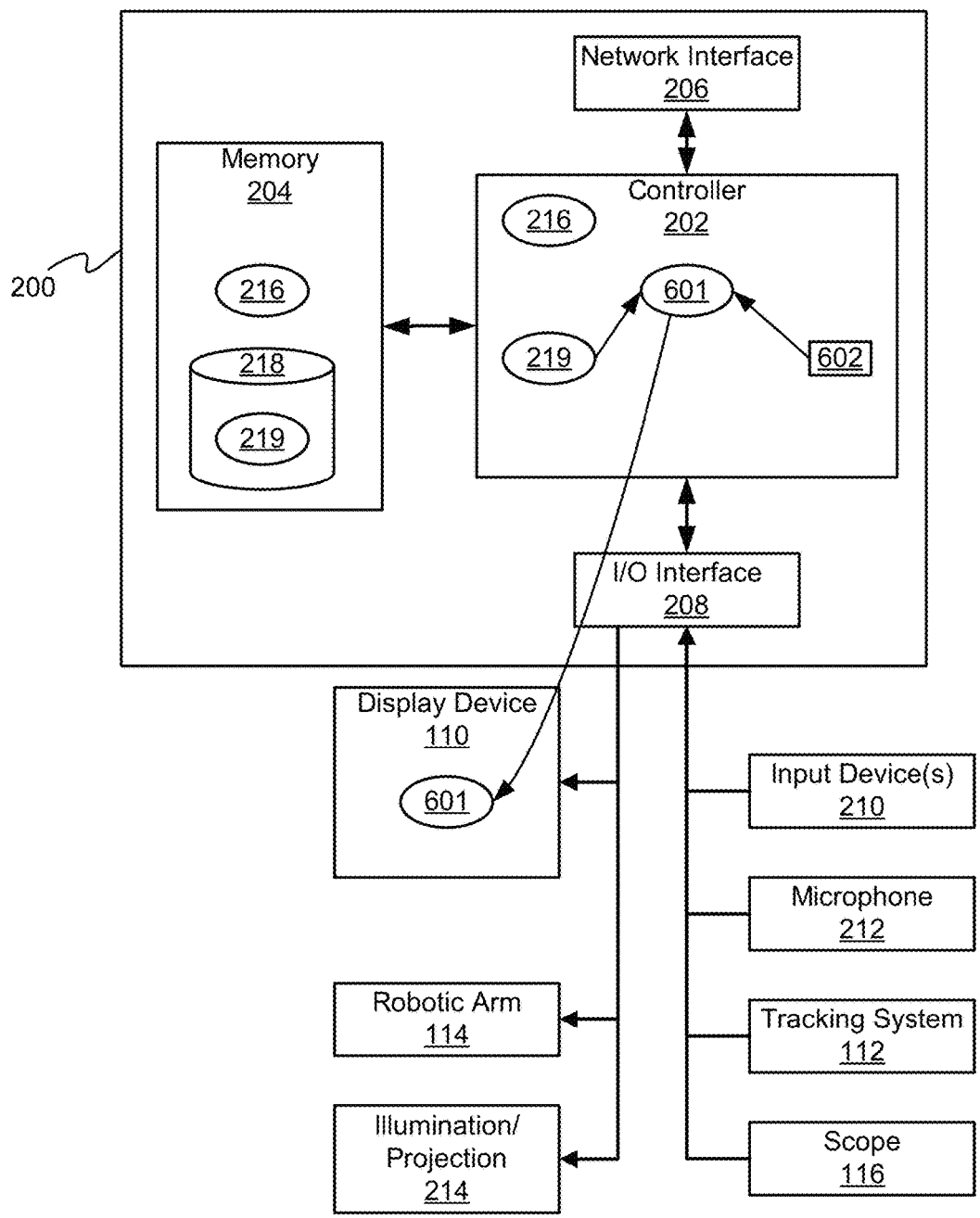
FIG. 6 depicts the device of FIG. 2 generating a first model of a surface using a given surface threshold value, according to a non-limiting embodiment.

Attention is next directed to FIG. 6, which is substantially similar to FIG. 2, with like elements having like numbers. However, in FIG. 6, controller 202 is implementing application 216 and specifically block 502 of method 500. In particular, controller 202 is generating a first model 601 of imaging data 219 using a given surface threshold value 602.

First model 601 can comprise, for example, a geometric model of imaging data 219 including, but not limited to, a polygon based mesh model and/or a three-dimensional mesh model and/or Bézier surface models and/or non-uniform rational B-spline (NURBS) models. Indeed, first model 601 can represents any three-dimensional model of a surface extracted from imaging data 219, for example skin surface. In general, the first model 601 includes smoothing, removal of artifacts and noise, and/or processing to make the model topologically conform to an expected surface anatomy (e.g. a head anatomy, a brain anatomy, and the like; indeed, as described in detail below, whether a head surface, a brain surface, and the like can be selected using the input device 210). Hence, the first model 601 is refined for use in a surgical procedure, but can require large processing and/or computation overhead.

Given surface threshold value 602 can comprise a value of an imaging signal intensity value that corresponds to a given surface type in imaging data 219. For example, when imaging data 219 comprises MR imaging data, given surface threshold value 602 can comprise an MM signal intensity value that corresponds to an estimate of a skin surface of patient 104. Determination of given surface threshold value 602 can be based on a statistical analysis of volumetric imaging data 219 (e.g. that attempts to distinguish surfaces of a patient based on given rules) using application 216, and/or given surface threshold value 602 may be received via input device 210. While present embodiments are described with respect to given surface threshold value 602 comprising an MM signal intensity that corresponds to skin of patient 104, given surface threshold value 602 can be set to other MRI signal intensities that correspond to estimates of other types of surfaces in patient 104 including, but not limited to, to an estimate of a brain surface and/or a cortical surface of patient 104.

FIG. 6 further depicts controller 202 controlling display device 110 to render first model 601 of imaging data 219 showing depth positions corresponding to given surface threshold value 602. Put another way, the depth positions depicted in FIG. 6 corresponding to given surface threshold value 602 comprise an extracted surface from imaging data 219 and/or a surface extracted from imaging data 219 using a mesh algorithm, and the like.

Figure 7:
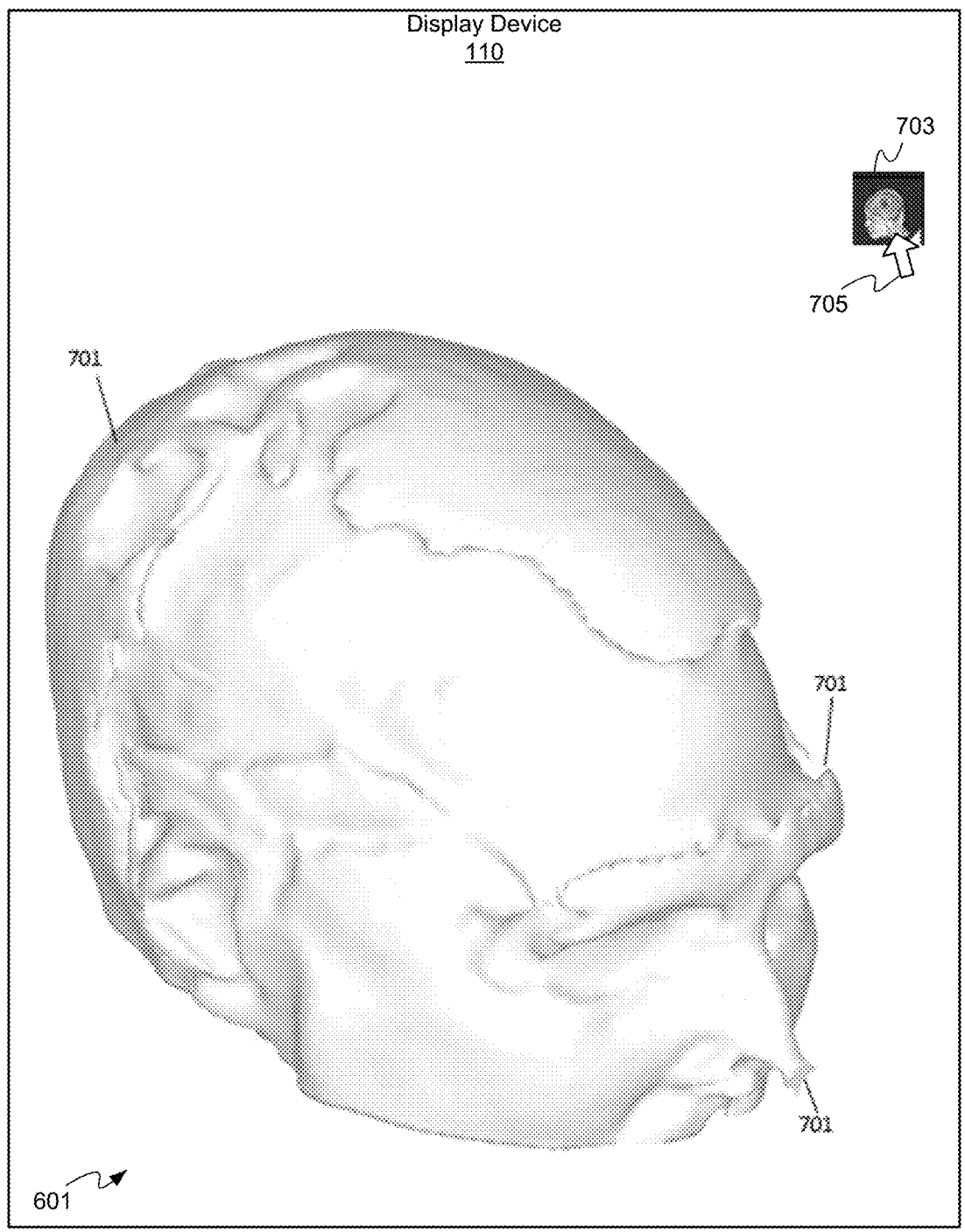
FIG. 7 depicts a display device controlled to render the first model of a surface, according to a non-limiting embodiment.

For example, attention is next directed to FIG. 7, which depicts display device 110 being controlled to render first model 601 and specifically a head of patient 104. However, as is clearly seen in FIG. 7, first model 601 includes various inaccuracies 701 as compared to the actual skin of patient 104. For example, a rendering of the nose is poorly defined; further inaccuracies 701 include various pits and/or bumps and/or craters and/or artifacts in the skin surface which can be due to MM signal inhomogeneity during an MM scan of patient 104.

While given surface threshold value 602 can be updated and in turn first model 601 can be regenerate and re-rendered to show an updated estimate of skin surface, each instance of generating first model 601 can result in a large and inefficient use of processing resources at device 200. For example, when first model 601 comprises a mesh model, generation of such mesh models can be extremely time consuming (e.g. on the order of tens of seconds), especially when the mesh model is applied to large data sets that are typical MM. While this issue could be at least partially addressed by using faster processors, and/or parallel processors and/or more processors, and the like, at device 200, such an increase in processing resources is expensive and/or inefficient, and further requires more power to operate. Furthermore, such an upgrade in processing resources may not be feasible.

Hence, as also depicted in FIG. 7, controller 202 controls display device 110 to render a virtual control 703 which, when actuated (for example, using a pointer 705), causes device 200 and/or controller 202 to operate more efficiently to update the given surface threshold value 602 as described hereafter. It will be assumed hereafter that when pointer 705 is used to actuate virtual controls, and the like, at display device 110, pointer 705 is being controlled by receipt of input at input device 210.

Figure 8:
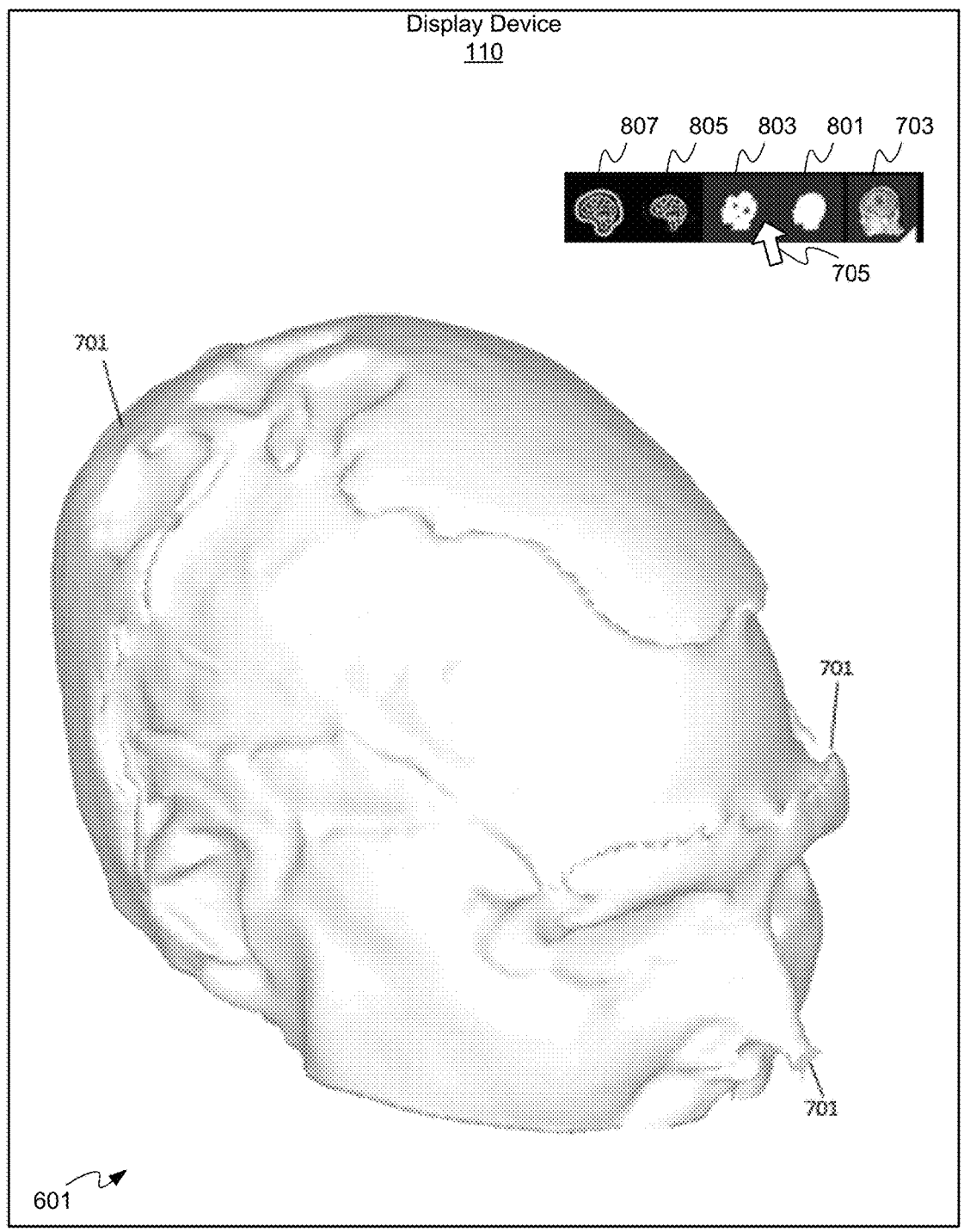
FIG. 8 depicts input being received to initiate rendering of a second model of the surface, the second model being of a type that is faster to compute than the first model, according to a non-limiting embodiment.

For example, attention is next directed to FIG. 8, which is substantially similar to FIG. 7, with like elements having like numbers. However, in FIG. 8, the virtual control 703 has been actuated which causes controller 202 to render four further virtual controls 801, 803, 805, 807. Actuation of virtual control 801 will cause controller 202 to control display device 110 to return to rendering first model 601 as depicted in FIG. 7 and/or cause controller 202 to control display device 110 to render first model 601 using an updated surface threshold value, determination of updated surface threshold values being described below.

Similarly, actuation of virtual control 805 will cause controller 202 to control display device 110 to render first model 601, however using a given surface threshold value comprising an MRI signal intensity that corresponds to the cortical surface of the brain of patient 104. In other words, in surgeries on a head of a patient, registration of outer skin of the patient and registration of a cortical surface of a brain of a patient are often the most used; hence, device 200 is specifically configured to provide convenient access to rendering both outer skin (e.g. via virtual control 801) of a patient and cortical surface of a brain (e.g. via virtual control 805) of a patient.

However, actuation of virtual controls 803, 807 will cause controller 202 to change a respective termination threshold using a second model, as described hereafter. While only actuation of virtual control 803 will be described in detail with respect to updating skin registration, actuation of virtual control 807 will cause controller 202 to operate in a similar manner, however with respect to cortical surface registration. Hence, as further depicted in FIG. 8, pointer 705 is actuating virtual control 803 which, in turn, causes controller 202 to implement block 504 of method 500.

Figure 9:
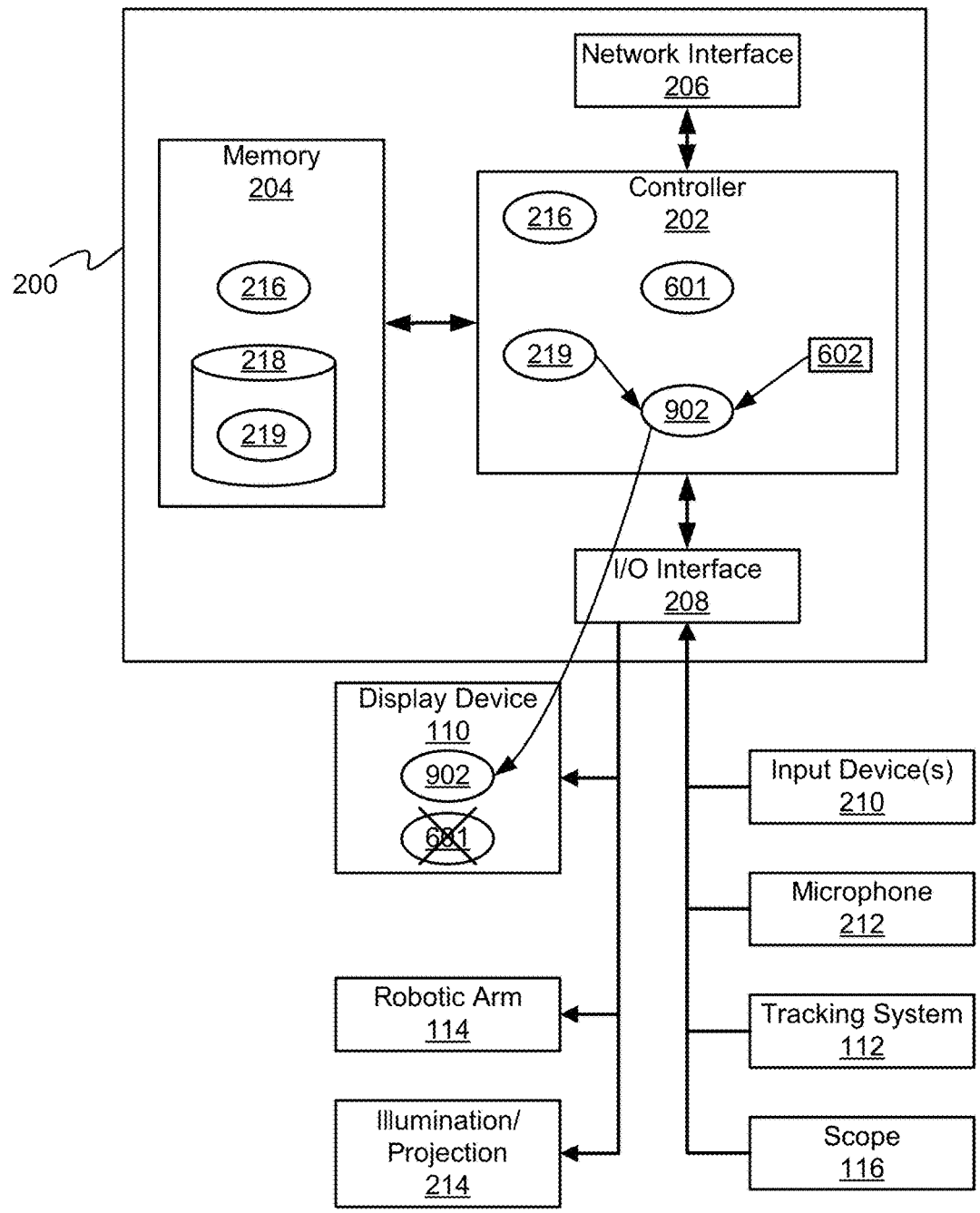
FIG. 9 depicts the device of FIG. 2 generating the second model of the surface using the given surface threshold value, according to a non-limiting embodiment.

For example, attention is next directed to FIG. 9, which is substantially similar to FIG. 2, with like elements having like numbers. However, in FIG. 6, controller 202 is implementing block 504 of method 500. In particular, controller 202 is generating a second model 902 of imaging data 219 using given surface threshold value 602.

Second model 902 can comprise a model of imaging data 219 that is faster to compute, as compared to first model 601, for example, a ray-casting model of imaging data 219. Such ray-casting models are generally faster to implement than the above described geometric (e.g. mesh) models and they may be computed on a graphics card, and the like. For example, ray-casting models are generally not as refined as geometric models. For example ray-casting models are not topologically closed with respect to, for example, head anatomy (e.g. a head surface), brain anatomy (e.g. a brain surface) and the like, and can have "floating" artifacts that can potentially cause problems with registration. Furthermore, such ray-casting models generally don't include validation. Hence, such ray-casting models are generally unsuitable for use in surgeries, however such ray-casting models are faster to compute than the geometric models of the first model 601, which are, in contrast closed topologically and are validated. Hence, the first model 601 is generally more refined than the second model 902 and/or the second model 902 is not refined as compared to the first model 601.

However, as such a ray-casting model can be generated from the same imaging data 219 as a mesh model, and further uses the same termination thresholds to estimate surfaces (e.g. by using termination thresholds to terminate rays of a ray-casting model), determining the effect of updating a surface threshold value on surface extraction from imaging data 219 occurs faster with a ray-casting algorithm than with a mesh algorithm.

Figure 10:
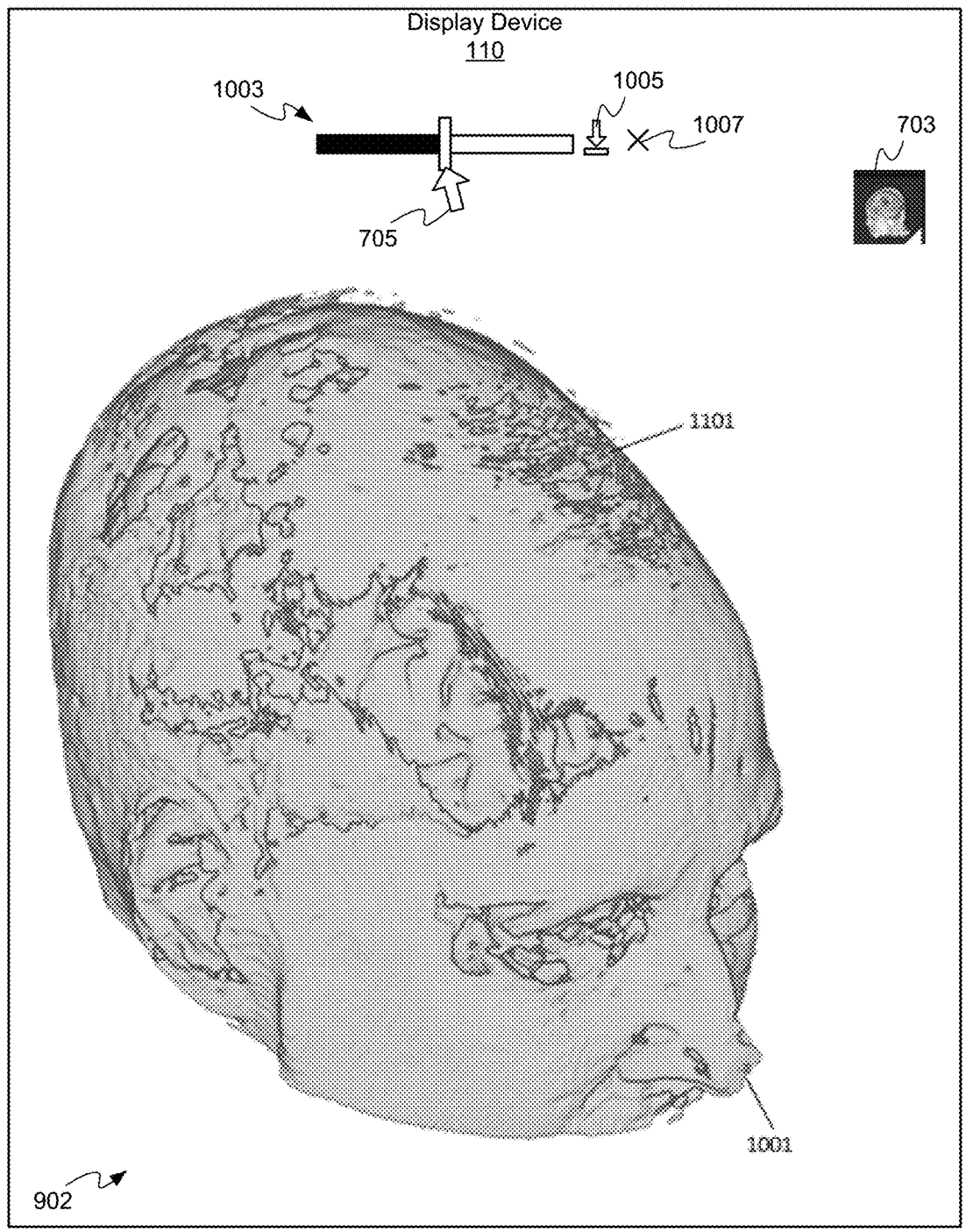
FIG. 10 depicts the display device controlled to render the second model of the surface using the given surface threshold value, according to a non-limiting embodiment.

Hence, as also depicted in FIG. 9, controller 202 is controlling display device 110 to replace first model 601 (e.g. a mesh model) with second model 902 (e.g. a ray-casting model) of imaging data 219, second model 902 showing respective depth positions corresponding to given surface threshold value 602, and second model 902 being of type that is faster to compute than first model 601, For example, attention is next directed to FIG. 10, which is substantially similar to FIG. 8, with like elements having like numbers. However, in FIG. 10, display device 110 is being controlled to render second model 902 rather than first model 601. Put another way, second model 902 has replaced first model 601 at display device 110 as compared to FIG. 8.

Put another way, the depth positions depicted in FIG. 10 corresponding to given surface threshold value 602 comprise an extracted surface from imaging data 219 and/or a surface extracted from imaging data 219 using a ray-casting algorithm, and the like.

Indeed, further comparing FIG. 10 and FIG. 8, controller 202 has aligned the rendering of first model 601 and second model 902 at display device 110. In particular, the position and/or angle of second model 902 rendered at display device 110 as depicted in FIG. 10, is the same and/or similar as the position and/or angle of first model 601 rendered at display device 110 as depicted in FIG. 9. Indeed, in FIG. 8, the position and/or angle of first model 601 may be adjusted using pointer 705 and when virtual control 803 is actuated, controller 202 replaces first model 601 with second model 902 at display device 110, second model 902 aligned with first model 601.

As also depicted in FIG. 10, second model 902 includes various inaccuracies 1001 of skin extraction similar to various inaccuracies 701. Indeed, further comparing FIG. 10 and FIG. 8, second model 902 being of type that is faster to compute than first model 601. Hence, while second model 902 has a different appearance due, for example, a different technique for surface extraction, the extracted surface of FIG. 10 is similar to the extracted surface of FIG. 8.

As also depicted in FIG. 10, and further as a result of actuation of virtual control 803, controller 202 controls display device 110 to stop rendering of virtual controls 801, 803, 805, 807, and renders a further virtual control, for example a slider 1003 which is used to change a surface threshold value as described below. Slider 1003 may be controlled using pointer 705. However, present embodiments are not limited to sliders, and any type of input and/or input device may be used to change a surface threshold value including, but not limited to, an editable numeric field, and the like.

As also depicted in FIG. 10, controller 202 further controls display device 110 to render virtual controls 1005, 1007. Virtual control 1005, when actuated, causes controller 202 to accept an updated surface threshold value as changed using slider 1003, and virtual control 1007, when actuated, causes controller 202 to cancel changing of the surface threshold value.

Figure 11:
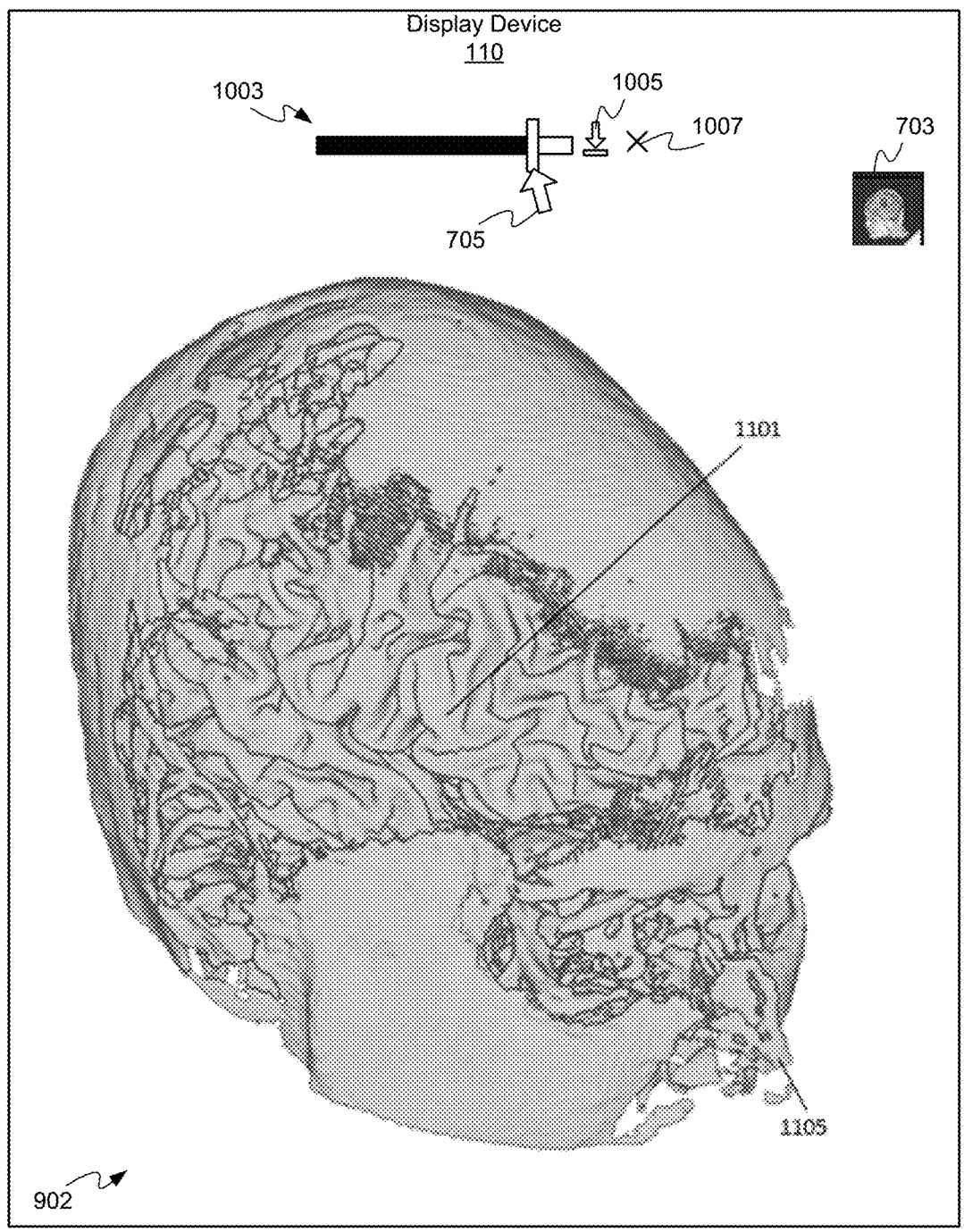
FIG. 11 depicts the surface threshold value being adjusted at the display device using the second model of the surface, according to a non-limiting embodiment.

Attention is next directed to FIG. 11, which is substantially similar to FIG. 10, with like elements having like numbers. However, in FIG. 11, input is being received (e.g. via pointer 705 adjusting slider 1003, as controlled via input device 210), the input changing given surface threshold value 602 to an updated surface threshold value.

For example, comparing FIG. 11 with FIG. 10, slider 103 is further to the right which causes a surface threshold value to be updated to an MM signal intensity value that corresponds to deeper surface position in the head of patient 104 than the initial given surface threshold value 602.

In particular, controller 202 controls display device 110 to update rendering of second model 902 to show updated respective depth positions corresponding to an updated surface threshold value as selected using slider 1003. In other words, another surface is extracted from imaging data 219 using a ray-casting algorithm.

For example, as depicted in FIG. 11, a rendering of a brain 1101 in imaging data 219 is visible, and furthermore in a region 1105 of the nose in imaging data 219, there are holes in second model 902, as there is space inside the nose in imaging data 219, which has become visible with an adjusted surface threshold value.

However, slider 1003 may also be moved in an opposite direction. For example, attention is next directed to FIG. 12, which is substantially similar to FIG. 1, with like elements having like numbers. However, in FIG. 12, input is being received (e.g. via pointer 705 adjusting slider 1003, as controlled via input device 210) which causes slider 103 to move left, which in turn causes a surface threshold value to be updated to an MRI signal intensity value that corresponds to less deep surface position in the head of patient 104 as compared to FIG. 11.

In particular, controller 202 controls display device 110 to update rendering of the second model 902 to show updated respective depth positions corresponding to an updated surface threshold value as selected using slider 1003.

Figure 12:
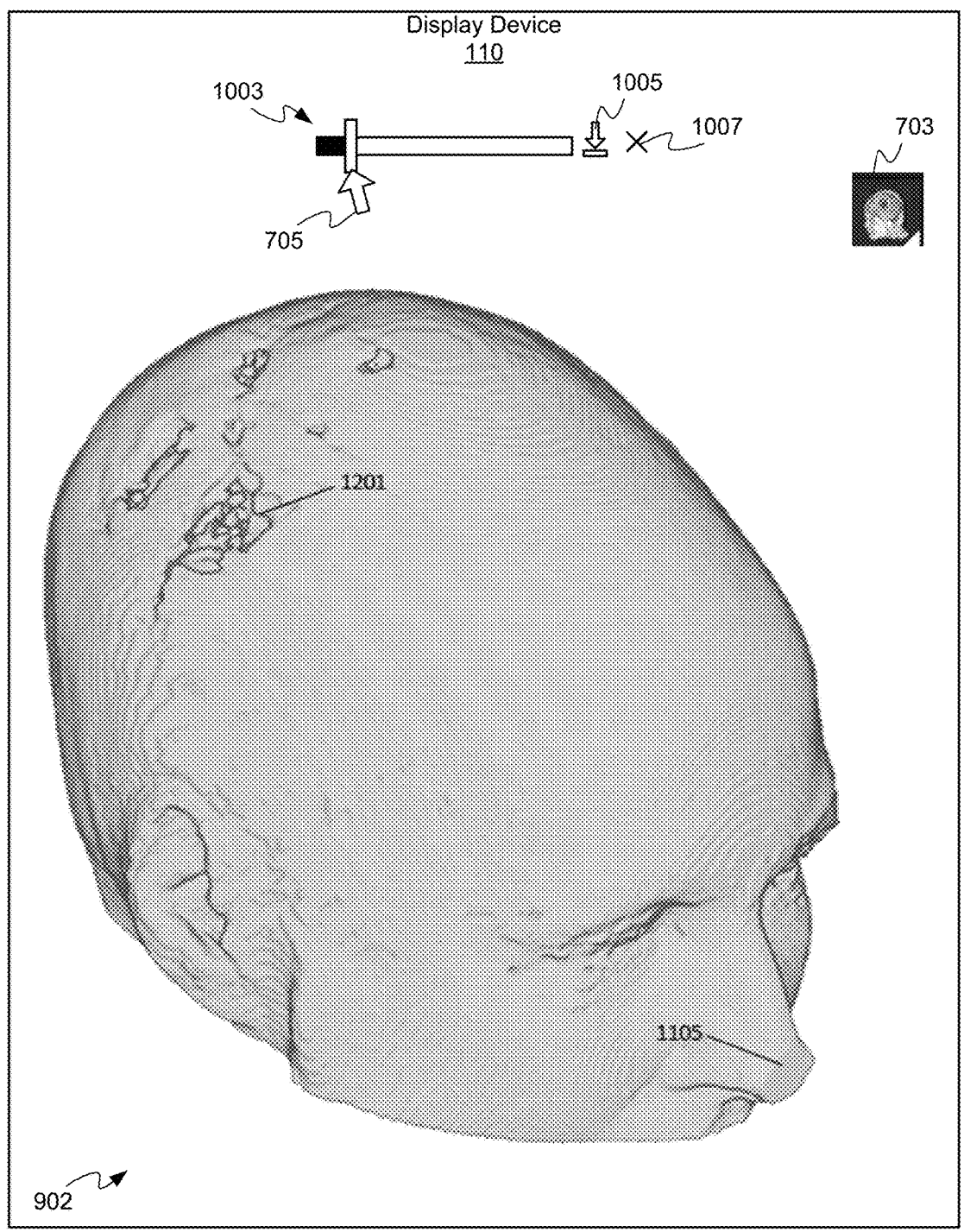
FIG. 12 depicts the surface threshold value being further adjusted at the display device using the second model of the surface, according to a non-limiting embodiment.

For example, as depicted in FIG. 12, a rendering of brain 1101 is no longer visible, and furthermore in region 1105 of the nose in imaging data 219, the nose is solid; though a tip of the nose is cut off, such a cut off may be irrelevant when planning a surgery. Furthermore, comparing FIG. 12 with FIG. 10, it is apparent that there are fewer inaccuracies, though a few inaccuracies 1201 remain, which can be due to MRI signal inhomogeneity, instrumentation issues, physical incisions, and the like. However, a majority of the extracted skin surface in the rendering of second model 902 in FIG. 12 is free of inaccuracies 1201. Furthermore, pointer 705 may be used to rotate and/or reposition the rendering of second model 902 to provide a visual inspection of second model 902 from various angles and/or to view inaccuracies on others sides of the extracted skin surface.

In this manner, using slider 1003, the effect of changing and/or updating the surface threshold value can be determined using second model 902, until an acceptance of an updated surface threshold value is received via an actuation of virtual control 1005. Furthermore, as second model 902 is of a type that is faster to compute than first model 601 (and/or as a ray-casting algorithm is faster than a mesh algorithm), each instance of updating of the surface threshold value causes second model 902 to be rendered in a time that is faster than if first model 601 were being rendered, making device 200 operate more efficiently than if first model 601 were being used to evaluate and/or update the surface threshold value. Indeed, in a successful prototype, each updating of second model 902 (e.g. using a ray-casting algorithm for second model 902) occurred in a time on the order of <100 ms, whereas each updating of first model 601 occurred in a time on the order of 30-60 seconds (e.g. using a mesh algorithm for first model 601).

Figure 13:
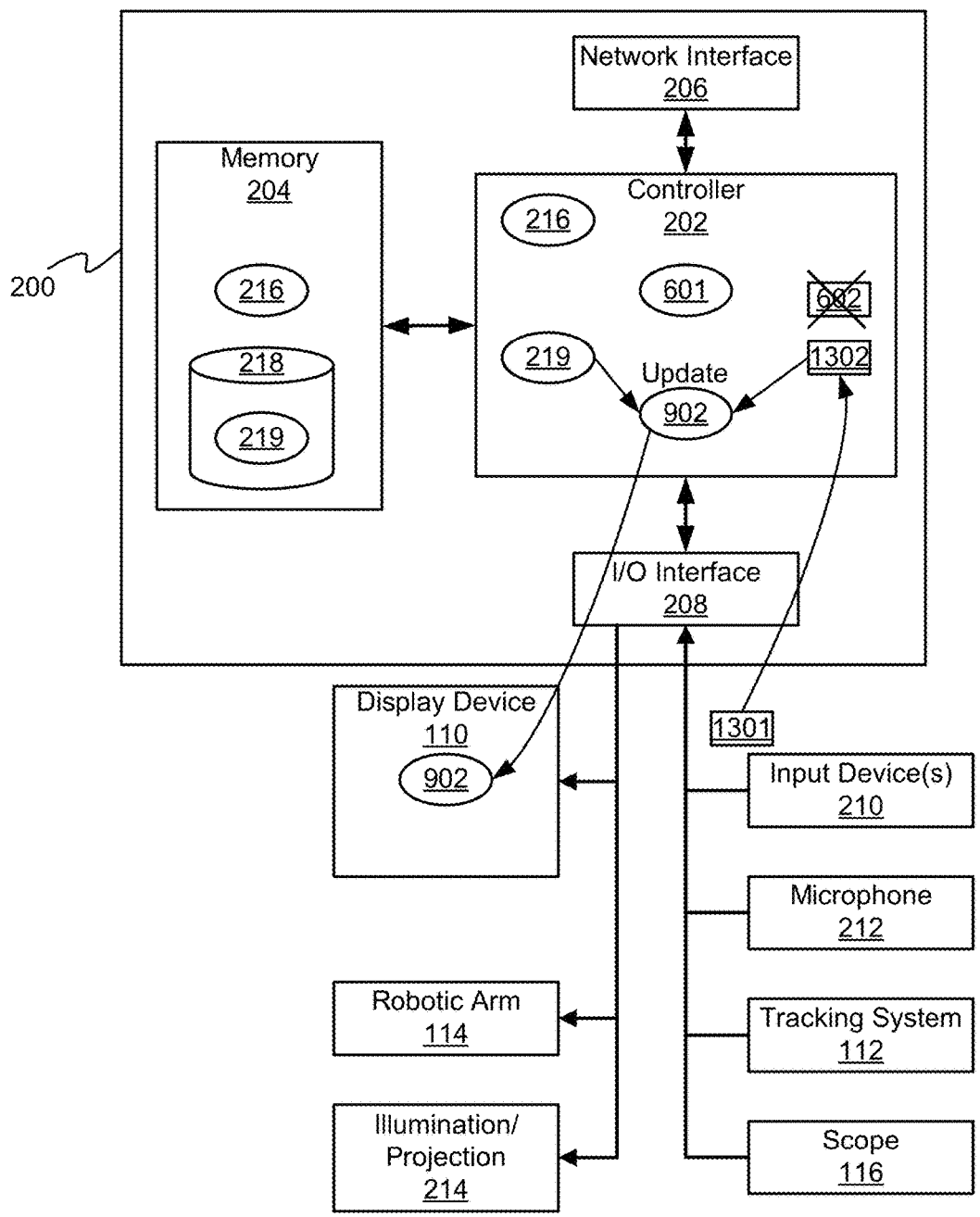
FIG. 13 depicts the device of FIG. 2 updating the surface threshold value, according to a non-limiting embodiment.

Furthermore, FIG. 11 and FIG. 12 depict an example embodiment of block 506 of method 500. Indeed, attention is next directed to FIG. 13, which is substantially similar to FIG. 10, with like elements having like numbers. However, FIG. 13 depicts controller 202 implementing block 506 of method 500. In particular, controller 202 is receiving input 1301 from input device 210 which changes the given surface threshold value 602 to an updated surface threshold value 1302, which is used to update second model 902 of imaging data 219 as depicted in FIG. 11 and FIG. 12. In other words, input 1301 corresponds to slider 1003 being moved left and/or right, with updated surface threshold value 1302 being changed accordingly.

Similarly, in FIG. 13, controller 202 is controlling display device 110 to update rendering of the second model 902 to show updated respective depth positions corresponding to updated surface threshold value 1302, similar to as described above with respect to FIG. 11 and FIG. 12.

Figure 14:
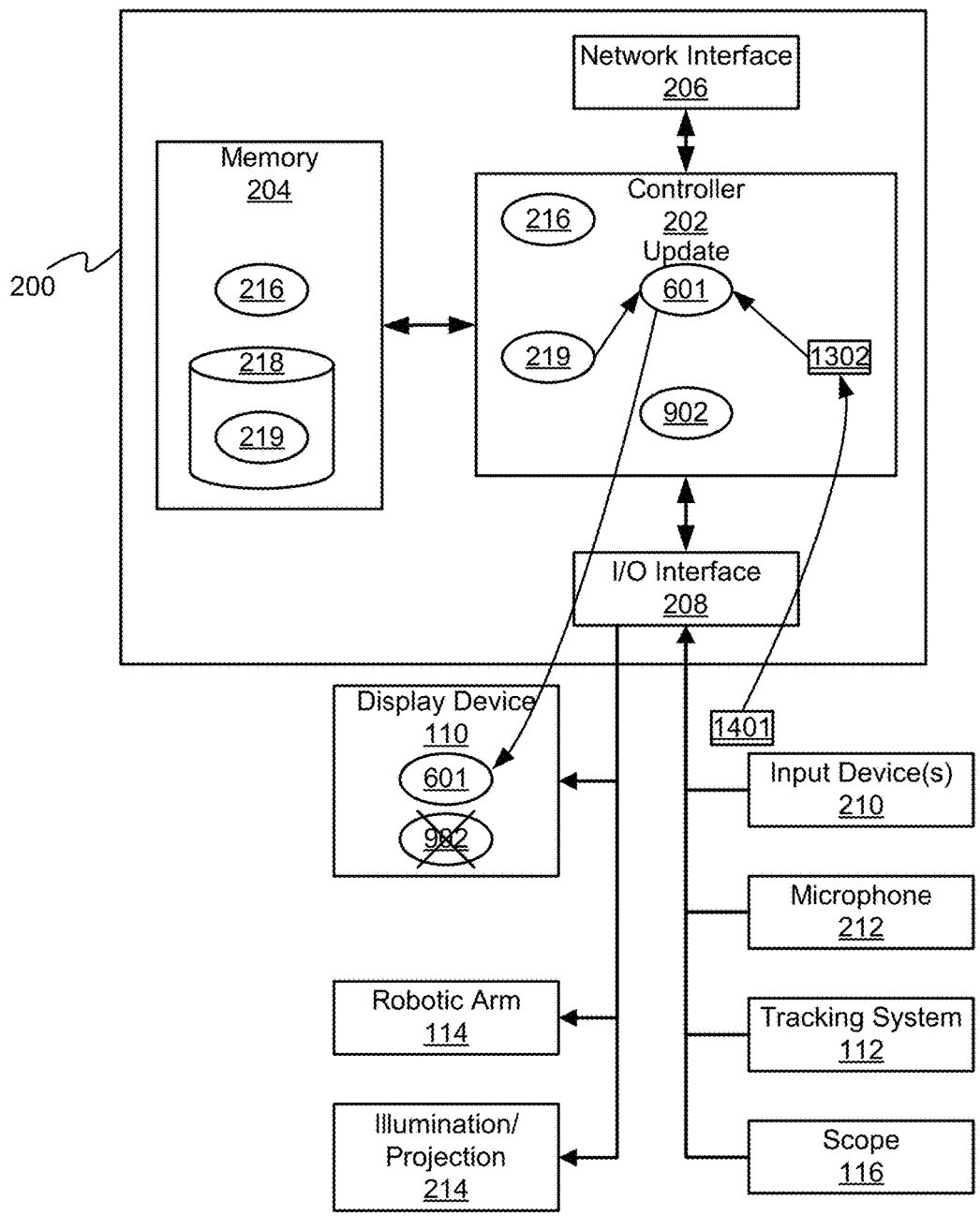
FIG. 14 depicts the device of FIG. 2 updating the first model using an updated surface threshold value, according to a non-limiting embodiment.

Attention is next directed to FIG. 14, which is substantially similar to FIG. 13, with like elements having like numbers. However, FIG. 14 depicts controller 202 implementing blocks 508, 510 of method 500. In particular, in FIG. 14, controller 202 is receiving, from input device 210, input 1401 indicating an acceptance of updated surface threshold value 1302 (e.g. corresponding to a surface threshold value selected in FIG. 12). Further in FIG. 14, controller 202 is updating first model 601 with updated surface threshold value 1302 selected using second model 902, and controlling display device 110 to replace second model 902 with first model 601 showing updated depth positions corresponding to the updated surface threshold value 1302. Indeed, FIG. 14 and FIG. 9 further illustrate that controller 202 is further configured to exchange given surface threshold value 602 and updated surface threshold value 1302 between first model 601 and second model 902.

Figure 15:
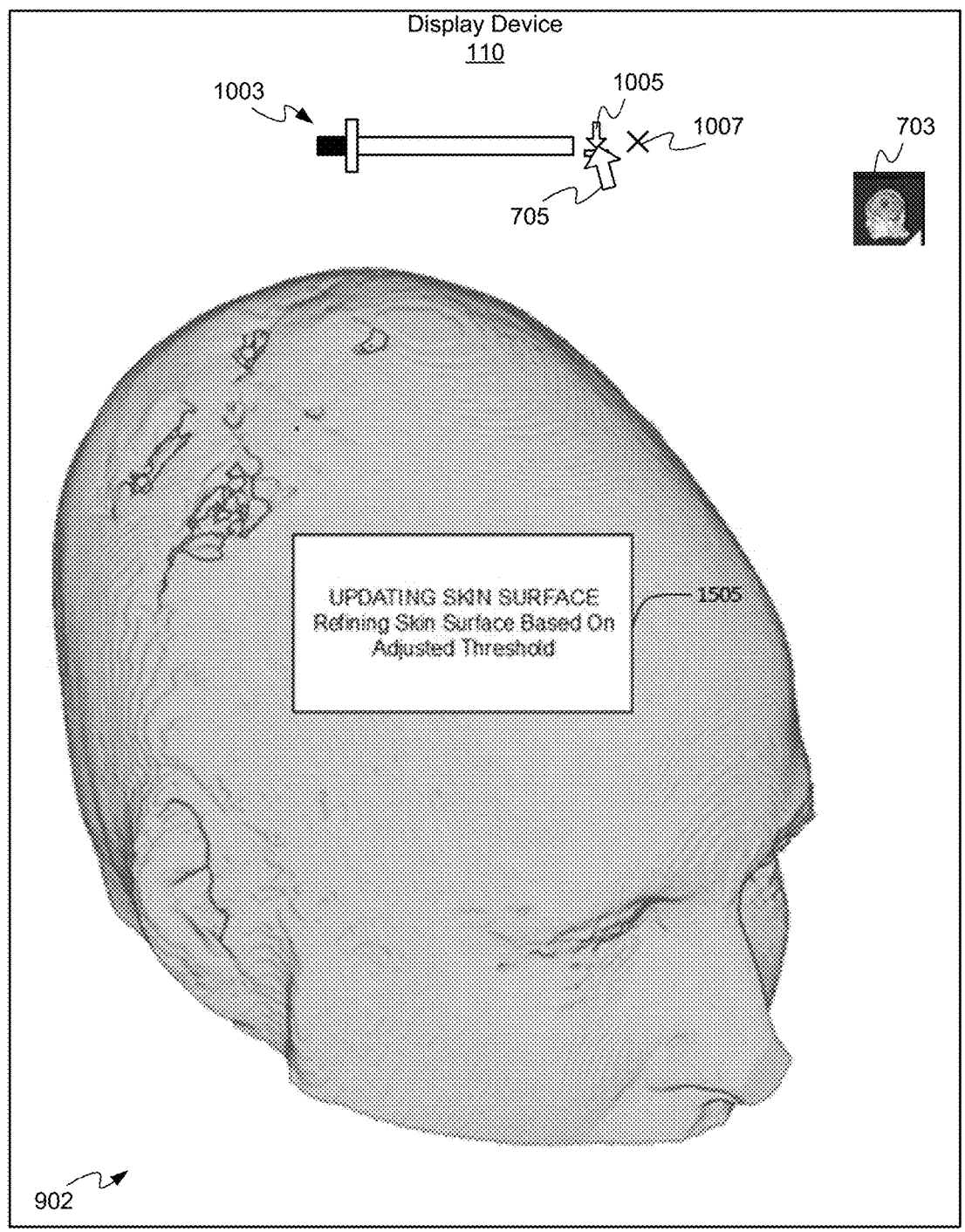
FIG. 15 depicts the display device during updating of the first model using an updated surface threshold value, according to a non-limiting embodiment.

Attention is next directed to FIG. 15 which is substantially similar to FIG. 12, with like elements having like numbers. However, in FIG. 15, block 508 has occurred via pointer 705 selecting virtual control 1005 to generate input 1401 and/or an acceptance of updated surface threshold value 1302. In response, block 510 is being implemented to control display device 110 to replace second model 902 with first model 601 showing updated depth positions corresponding to updated surface threshold value 1302. However, as second model 902 is of higher resolution than second model 902, first model 601 takes more time and/or processing resources to update, and hence when virtual control 1005 is selected, second model 902 remains at display device 110 for the time needed to update first model 601.

In the example depicted in FIG. 15, controller 202 optionally controls display device 110 to render a notification 1505 while first model 601 is being updated, notification 1505 indicating that first model 601 is being updated based on an updated (e.g. adjusted) surface threshold value. As the example embodiment is directed towards skin extraction, notification 1505 indicates "Updating Skin Surface" and the like. However, notification 1505 may be adapted accordingly when a cortical surface is being updated.

Once controller 202 updates first model 601 using updated surface threshold value 1302, controller 202 replaces second model 902 with updated first model 601 at display device 110.

Figure 16:
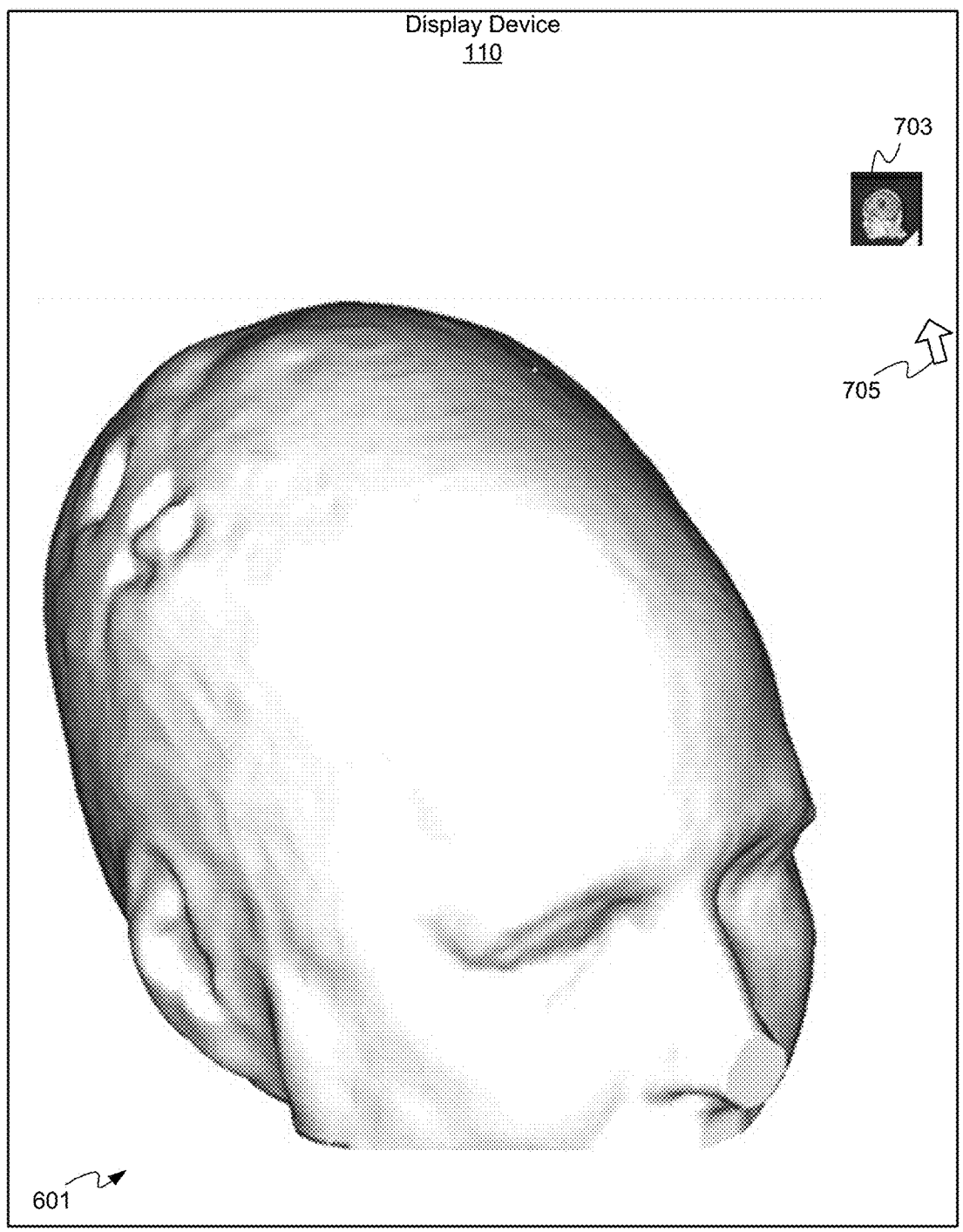
FIG. 16 depicts the display device controlled to render the first model of a surface as updated using the updated surface threshold value, according to a non-limiting embodiment.

For example, attention is next directed to FIG. 16 which is substantially similar to FIG. 15, with like elements having like numbers. However, in FIG. 16, block 510 has been implemented and controller 110 has controlled display device 110 to replace second model 902 with first model 601 updated to show updated depth positions corresponding to updated surface threshold value 1302.

For example, first model 601 depicted in FIG. 16 is similar to second model 902 as depicted in FIG. 12 and FIG. 15, but at a higher resolution and generated using updated surface threshold value 1302 selected using second model 902 and slider 1003. Furthermore, slider 1003 has been removed. Method 500 can be repeated, however, upon actuation of virtual control 703. Furthermore, second model 902 may be rotated and the like using pointer 705, for example to plan a surgical procedure.

Hence, described herein is a method, system and apparatus for surface rendering using medical imaging data that may result in an image rendering device, such as device 200, to operate more efficiently in selecting an updated surface threshold value during surface extraction. For example, an extraction algorithm, and the like (e.g. application 216), is used to generate a skin surface, and the like, using a default threshold based on statistical analysis of volumetric imaging data 219. The skin surface is rendered at a display device according to a first model, such as a three-dimensional geometrical model and/or a mesh surface. To adjust the threshold, the first model is replaced at the display device with a second model that is faster to compute than the first model, such as a ray-casting rendering of the volumetric imaging data using the default threshold to terminate the rays in the ray-casting model. The second model appears similar to the first model, but is not necessarily identical. The threshold is adjusted (e.g. using a slider, an editable numeric field, and the like), and the second model is dynamically adjusted at the display device. When an adjusted threshold is accepted, the adjusted threshold is used by the extraction algorithm to extract a new skin surface in order to replace the first model, which is then rendered at the display device.

Those skilled in the art will appreciate that in some embodiments, the functionality of the application 216 may be implemented using pre-programmed hardware or firmware elements (e.g., application specific integrated circuits (ASICs), electrically erasable programmable read-only memories (EEPROMs), etc.), or other related components.

The scope of the claims should not be limited by the embodiments set forth in the above examples, but should be given the broadest interpretation consistent with the description as a whole.

The invention claimed is:

1. A device for surface rendering using medical imaging data, the device comprising:
   a memory storing the medical imaging data,
   the medical imaging data comprising three-dimensional medical imaging data of an object that includes at least a first surface;
   a display device;
   an input device; and
   a controller that:
      control the display device to render a first model of the medical imaging data showing depth positions corresponding to a given surface threshold value, wherein the given surface threshold value comprising a medical imaging signal intensity value that corresponds to an estimate of the first surface of the object and wherein the given surface threshold value is determined based on a statistical analysis of a volumetric data by using an extraction application to distinguish surfaces of a patient base on given rules;
      control the display device to replace the first model with a second model of the medical imaging data showing respective depth positions corresponding to the given surface threshold value, wherein the second model being faster to compute than the first model, and wherein the first model removed from the display device when the second model replaces the first model at the display device the second model rendered at the display device in one or more of a similar position and a similar angle as the first model as rendered at the display device, such that rendering of the first model and the second model at the display device are aligned;
      receive, from the input device, input changing the given surface threshold value to an updated surface threshold value, and control the display device to update rendering of the second model to show updated respective depth positions corresponding to the updated surface threshold value, wherein the updated surface threshold value comprising a respective medical imaging signal intensity value that corresponds to a different surface position in the object than the medical imaging signal intensity value of the given surface threshold value;
      receive, from the input device, an acceptance of the updated surface threshold value;
      control the display device to replace the second model with the first model showing updated depth positions corresponding to the updated surface threshold value; and
   wherein the first model comprises a mesh model of the medical imaging data.

2. The device of claim 1, wherein the second model has not been refined as compared with the first model.

3. The device of claim 1, wherein the second model comprises a ray-casting model.

4. The device of claim 1, wherein the estimate of the first surface of the object comprises respective estimate of a skin surface or a brain surface of the object.

5. The device of claim 1, wherein the controller is further configured to exchange the given surface threshold value and the updated surface threshold value between the first model and the second model.

6. The device of claim 1, wherein the input changing the given surface threshold value to the updated surface threshold value comprises slider input received at a slider rendered at the display device.

7. The device of claim 1, wherein the medical imaging data is selected from a list comprising of computed tomography (CT) imaging data, positron emissions tomography (PET) imaging data and 3D surface scanner imaging data.

8. The device of claim 1, wherein the medical imaging data comprises magnetic resonance imaging data, and the medical imaging signal intensity value and the respective medical imaging signal intensity value each comprise a respective magnetic resonance imaging signal intensity value.

9. A method for surface rendering using medical imaging data, the method comprising:
controlling, using a controller, a display device to render a first model of the medical imaging data showing depth positions corresponding to a given surface threshold value, the medical imaging data comprising three-dimensional medical imaging data of an object that includes at least a first surface, the given threshold surface value comprising a medical imaging signal intensity value that corresponds to an estimate of the first surface of the object;
controlling, using a controller, the display device to replace the first model with a second model of the medical imaging data showing respective depth positions corresponding to the given surface threshold value, wherein the second model being faster to compute than the first model the first model removed from the display device when the second model replaces the first model at the display device, wherein the second model rendered at the display device in one or more of a similar position and a similar angle as the first model as rendered at the display device, such that rendering of the first model and the second model at the display device are aligned;
receiving, at the controller, from an input device, input changing the given surface threshold value to an updated surface threshold value, and controlling, using the controller, wherein the display device to update rendering of the second model to show updated respective depth positions corresponding to the updated surface threshold value, wherein the updated surface threshold value comprising a respective medical imaging signal intensity value that corresponds to a different surface position in the object than the medical imaging signal intensity value of the given surface threshold value, and wherein the given surface threshold value is determined based on a statistical analysis of a volumetric data by using an extraction application to distinguish surfaces of a patient base on given rules;
receiving, at the controller, from the input device, an acceptance of the updated surface threshold value; and
controlling, using the controller, the display device to replace the second model with the first model showing updated depth positions corresponding to the updated surface threshold value, wherein the first model comprises a mesh model of the medical imaging data.

10. The method of claim 9, wherein the second model has not been refined as compared with the first model.

11. The method of claim 9, wherein the second model comprises a ray-casting model.

12. The method of claim 9, wherein the estimate of the first surface of the object comprises respective estimate of a skin surface or a brain surface of the object.

13. The method of claim 9, further comprising exchanging, using the controller, the given surface threshold value and the updated surface threshold value between the first model and the second model.

14. The method of claim 9, wherein the input changing the given surface threshold value to the updated surface threshold value comprises slider input received at a slider rendered at the display device.

15. The method of claim 9, wherein the medical imaging data is selected from a list comprising of computed tomography (CT) imaging data, positron emissions tomography (PET) imaging data and 3D surface scanner imaging data.

16. The method of claim 9, wherein the medical imaging data comprises magnetic resonance imaging data, and the medical imaging signal intensity value and the respective medical imaging signal intensity value each comprise a respective magnetic resonance imaging signal intensity value.

* * * * *